(12) United States Patent
Agrawal

(10) Patent No.: US 6,624,293 B1
(45) Date of Patent: *Sep. 23, 2003

(54) MODIFIED PROTEIN KINASE A-SPECIFIC OLIGONUCLEOTIDES AND METHODS OF THEIR USE

(75) Inventor: Sudhir Agrawal, Shrewsbury, MA (US)

(73) Assignee: Hybridon, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/022,965

(22) Filed: Feb. 12, 1998

Related U.S. Application Data

(63) Continuation-in-part of application No. 08/532,979, filed on Sep. 22, 1995, now Pat. No. 5,969,117, which is a continuation-in-part of application No. 08/516,454, filed on Aug. 17, 1995, now Pat. No. 5,652,356.
(60) Provisional application No. 60/040,740, filed on Mar. 12, 1997.

(51) Int. Cl.[7] .................................................. C07H 19/00
(52) U.S. Cl. ..................... 536/22.1; 435/6; 536/23.1; 536/23.5; 536/24.3; 536/25.3; 536/25.7; 514/44
(58) Field of Search .................. 435/6; 536/22.1, 536/23.1, 23.5, 24.3, 25.3, 25.7; 514/44

(56) References Cited

U.S. PATENT DOCUMENTS

| | | | |
|---|---|---|---|
| 4,309,404 A | 1/1982 | DeNeale et al. | 424/21 |
| 4,309,406 A | 1/1982 | Guley et al. | 424/21 |
| 4,556,552 A | 12/1985 | Porter et al. | 424/32 |
| 4,704,295 A | 11/1987 | Porter et al. | 427/3 |
| 4,806,463 A | 2/1989 | Goodchild et al. | 435/5 |
| 5,149,797 A | 9/1992 | Pederson et al. | 536/27 |
| 5,194,428 A | 3/1993 | Agrawal et al. | 514/44 |
| 5,220,007 A | * 6/1993 | Pederson et al. | 536/23.1 |
| 5,271,941 A | * 12/1993 | Cho-Chung | 424/450 |
| 5,470,967 A | * 11/1995 | Huie et al. | 536/24.3 |
| 5,652,355 A | 7/1997 | Metelev et al. | 536/24.5 |
| 5,969,117 A | * 10/1999 | Agrawal | 536/22.1 |

FOREIGN PATENT DOCUMENTS

| | | | |
|---|---|---|---|
| DE | 41 10 085 A1 | 10/1992 | |
| EP | 0 490 077 A1 | 10/1991 | ........... C12N/15/11 |

(List continued on next page.)

OTHER PUBLICATIONS

Kabat and Mayer (eds.), "Experimental Immunochemistry, 2D Edition," pp. 135–240, Springfield, IL, CC Thomas (1961).

(List continued on next page.)

*Primary Examiner*—Jezia Riley
(74) *Attorney, Agent, or Firm*—Hale and Dorr LLP

(57) ABSTRACT

Disclosed are synthetic, modified oligonucleotides complementary to, and capable of down-regulating the expression of, nucleic acid encoding protein kinase A subunit $RI_\alpha$. The modified oligonucleotides have from about 15 to about 30 nucleotides and are hybrid, inverted hybrid, or inverted chimeric oligonucleotides. Also disclosed are therapeutic compositions containing such oligonucleotides and methods of using the same.

31 Claims, 1 Drawing Sheet

FOREIGN PATENT DOCUMENTS

| WO | WO 91/12323 | 8/1991 | |
|---|---|---|---|
| WO | WO 93/13114 | 7/1993 | |
| WO | WO 93/13121 | 7/1993 | |
| WO | WO 93/13740 | 7/1993 | |
| WO | WO 94/02498 | 2/1994 | |
| WO | WO 94/02499 | 2/1994 | |
| WO | WO 94/07367 | 4/1994 | |
| WO | WO 94/08003 | 4/1994 | |
| WO | WO 94/13685 | 6/1994 | |
| WO | 94/17189 | 8/1994 | C12N/15/54 |
| WO | 94/23028 | 10/1994 | C12N/15/11 |
| WO | WO 94/26887 | 11/1994 | |
| WO | WO 95/02069 | 1/1995 | |
| WO | WO 95/09236 | 4/1995 | |
| WO | 96/16976 | 6/1996 | C07H/21/02 |
| WO | 96/31600 | 10/1996 | C12N/15/11 |
| WO | 97/11171 | 3/1997 | C12N/15/11 |

OTHER PUBLICATIONS

Metelev et al. (1994) "Study of Antisense Oligonucleotide Phosphorthioates Containing Segments of Oligdeoxynucleotides and 2'-O-Methyloligonucleotides," *Bioorganic& Medicinal Chem. Lett.* 4:2929-2934.

Paterson et al. (1977) "Structural Gene Identification and Mapping by DNA mRNA Hybrid-Arrested Cell-Free Translation," *Proc. Natl. Acad. Sci. USA* 74:4370-4374.

Stephenson et al. (1978) "Inhibition of Rous Sarcoma Viral RNA Translation By A Specific Oligodeoxyribonucleotide," *Proc. Natl. Acad. Sci. USA* 75:285-288.

Agrawal et al. (1995) "Modified Oligonucleotides As Therapeutic And Diagostic Agents," *Curr.Opin. Biotech.* 6:12-19.

Agrawal et al. (1995) "Pharmacokinetics of Antisense Oligucleotides," *Clin. Pharmcokinet.* 28:7-16.

Krieg et al. (1995) "CpG Motifs In Bacterial DNA Trigger Direct B-Cell Activation," *Nature* 374:546-549.

Kandimalla et al. (1995) "Synthesis and Properties of 2'-O-Methylribonucleotide Metheylphosphonate Containing Chimeric Oligonucleotides," *Nucleosides and Nucleotides* 14:1031-1035.

Tao et al. (1995) "Uptake, Intracellular Distribution, and Stability of Oligodeoxynucleotide Phosphorothioate By *Schistosoma Mansoni*," *Antisense Res.& Dev.* 5:123-129.

Agrawal (ed.) "Antisense Therapeutics," *Meth. in Mol. Medicine,* Preface v, Humana Press, New Jersey (1996).

Zamecnik, Agrawal (ed.) "Antisense Therapeutics," *Meth. in Mol. Medicine,* p. 6, Humana Press, New Jersey (1996).

Monia et al. (1996) "Antitumor Activity of a Phosphorothioate Antisense Oligodeoxynucleotide Targeted Against C-*raf* Kinase," *Nature Med.* 2(6):668-675.

Craig et al. (1997) "Patent Strategies in the Antisense Oligonucleotide Based Therapeutic Approach," *Exp. Opin. Ther. Patents* 7(10):1175-1182.

Milner et al. (1997) "Selecting Effective Antisense Reagents On Combinatorial Oligonucleotide Arrays," *Nature Biotech.* 15:537-541.

Agrawal et al. (1998) "Mixed Backbone Oligonucleotides: Improvement in Oligonucleotide-Induced Toxicity Vivo," *Antisense& Nucl. Acid Drug Devel.* 8:135-139.

Zhou et al. (1998) "Mixed Backbone Oligonucleotides As Second-Generation Antisense Agents With Reduced Phosphorothioate-Related Side Effects," *Bioorg.& Med. Chem. Lett.* 8:3269-3274.

Chen et al. "Phase I Evaluation of GEM 231, A Second Generation Oligonucleotide Targeted At Type I Protein Kinase A (PKA-I) In Patients With Refractory Solid Tumors," Abstract.

Cho-Chung, YS, "Role of cyclic AMP receptor proteins in growth, differentiation, and suppression of malignancy: new approaches to therapy." *Cancer Res.,* vol. 50, pp. 7093-7100 (1990).

Cho-Chung et al., *Curr. Opin. Thera. Patents,* vol. 3, pp. 1737-1750 (1993).

Lohmann and Walter, "Regulation of the Cellular and Subcellular Concentrations and Distribution of Cyclic Nucleotide-Dependent Protein Kinases." *Advances in Cyclic Nucleotide and Protein Phosphorylation Research,* vol. 18, pp. 63-117, Raven, New York, (1984).

Monia et al., "Evaluation of 2'—Modified Oligonucleotides Containing 2'-Deoxy Gaps as Antisense Inhibitors of Gene Expression." *Journal of Biological Chemistry,* vol. 268, pp. 14514-14522 (1993).

Nesterova and Cho-Chung "A single-injection protein kinase A-directed antisense treatment to inhibit tumor growth." *Nature Med.,* vol. 1, pp. 528-533 (1995).

Pisetsky et al., "Stimulation of in vitro proliferation of murine lympocytes by synthetic oligodeoxynucleotides" *Molecular Biology Reports,* vol. 18, pp. 217-221 (1993).

Zamecnik and Stephenson, "Inhibition of Rous sarcoma virus replication and cell transformation by a specific oligodeoxynucleotide." *Proc. Natl. Acad. Sci.* (USA), vol. 75, pp. 280-284 (1978).

Zhang et al., "In Vivo Stability, Disposition and Metabolism of a "Hybrid" Oligonucleotide Phosphorothioate in Rats" *Biochemical Pharmacology,* vol. 50, pp. 545-556 (1995).

Agrawal, et al., "Absorption, Tissue Distribution and *In Vivo*Stability in Rats of a Hybrid Antisense Oligonucleotide Following Oral Administration", Biochemical Pharmacology, vol. 50, No. 4, pp. 571-576 (1995).

Hoke, et al., "Effects of phosphorothioate capping on antisense oligonucleotide stability, hybridization, and antiviral efficacy versus herpes simplex virus infection", Nucleic Acids Research, vol. 19, No. 20, pp. 5743-5748 (1991).

Lu, et al. "Chemically Unambiguous Peptide Immunogen: Preparation, Orientation and Antigenicity of Purified Peptide Conjugated to the Multiple Antigen Peptide System", Molecular Immunology, vol. 28, No. 6, pp. 623-630 (1991).

Vlassov et al., "*In Vivo*Pharmacokinetics of Oligonucleotides Following Administration by Different Routes", *Delivery Strategies for Antisense Oligonucleotide Therapeutics* (Akhtar Ed.), CRC Press, pp. 71-83, (1995).

Zhang, et al., "Pharmacokinetics of an anti-human immunodeficiency virus antisense oligodeoxynucleotide phosphorotioate (GEM 91) in HIV-infected subjects", Clinical Pharmacology & Therapeutics, vol. 58, No. 1, pp. 44-53 (1995).

Zhao, et al., "Comparison of Cellular Binding and Uptake of Antisense Phosphodiester, Phosphorothioate, and Mixed Phosphorothioate and Methylphosphonate Oligonucleotides", Antisense Research and Development, 3:53-66 (1993).

Agrawal; "*In Vivo* Pharmacokinetics of Oligonucleotides"; in *Applied Antisense Oligonucleotide Technology* (Stein and Kreig, Eds.); pp. 365-385 (1998).

Agrawal, et al; "Comparative Pharmacokinetics of Antisense Oligonucleotides"; in *Methods in Molecular Medicine: Antisense Therapeutics (Agrawal, Ed.)* ; pp. 247–270 (1996).

Cho–Chung, et al.; "Protein Kinase–A Directed Antisense Therapy of Tumor Growth *In Vivo*"; in *Methods in Molecular Medicine: Antisense Therapeutics (Agrawal, Ed.)*; pp. 213–224 (1996).

Leff; "Italian Oncologists Test Hybridon's Antisense, Molecules in Nude Mice"; BioWorld Today; vol. 8, No. 223, pp. 1, 4 (1997).

* cited by examiner

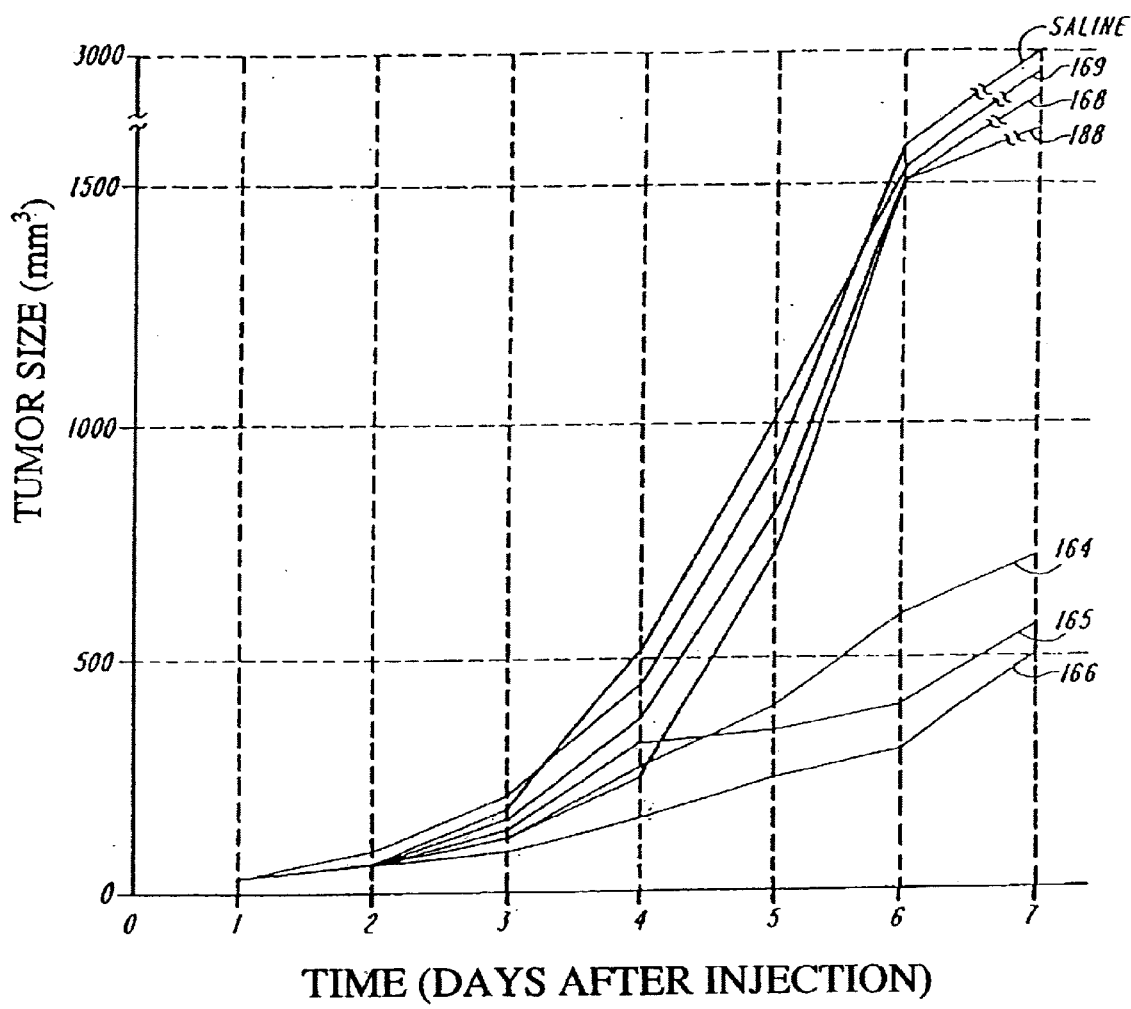

SEQUENCE LISTING

```
<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:
      complementary oligonucleotide to the rev gene of HIV-1

<400> SEQUENCE: 1
tcgtcgctgt ctccgcttct tcttgcc                                        27

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:CpG in
      HYB-0272

<400> SEQUENCE: 2
tccatgacgt tcctgatgct ttttggggg                                      29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:GpC in
      HYB-0352

<400> SEQUENCE: 3
tccatgagct tcctgatgct ttttggggg                                      29
```

MODIFIED PROTEIN KINASE A-SPECIFIC OLIGONUCLEOTIDES AND METHODS OF THEIR USE

This application claims the benefit of U.S. Ser. No. 60/040,740, filed on Mar. 12, 1997, and is a continuation-in-part of U.S. Ser. No. 08/532,979, filed Sep. 22, 1995, (now U.S. Pat. No. 5,969,117), which is a continuation-in-part of U.S. Ser. No. 08/516,454, filed Aug. 17, 1995 (now U.S. Pat. No. 5,652,356).

FIELD OF THE INVENTION

The present invention relates to cancer therapy. More specifically, the present invention relates to the inhibition of the proliferation of cancer cells using modified antisense oligonucleotides complementary to nucleic acid encoding the protein kinase A $RI_\alpha$ subunit.

BACKGROUND OF THE INVENTION

The development of effective cancer therapies has been a major focus of biomedical research. Surgical procedures have been developed and used to treat patients whose tumors are confined to particular anatomical sites. However, at present, only about 25% of patients have tumors that are truly confined and amenable to surgical treatment alone (Slapak et al. in Harrison's Principles of Internal Medicine (Isselbacher et al., eds.) McGraw-Hill, Inc., NY (1994) pp. 1826–1850). Radiation therapy, like surgery, is a local modality whose usefulness in the treatment of cancer depends to a large extent on the inherent radiosensitivity of the tumor and its adjacent normal tissues. However, radiation therapy is associated with both acute toxicity and long term sequelae. Furthermore, radiation therapy is known to be mutagenic, carcinogenic, and teratogenic (Slapak et al., ibid.).

Systemic chemotherapy alone or in combination with surgery and/or radiation therapy is currently the primary treatment available for disseminated malignancies. However, conventional chemotherapeutic agents which either block enzymatic pathways or randomly interact with DNA irrespective of the cell phenotype, lack specificity for killing neoplastic cells. Thus, systemic toxicity often results from standard cytotoxic chemotherapy. More recently, the development of agents that block replication, transcription, or translation in transformed cells, and at the same time defeat the ability of cells to become resistant, has been the goal of many approaches to chemotherapy.

One strategy is to down regulate the expression of a gene associated with the neoplastic phenotype in a cell. A technique for turning off a single activated gene is the use of antisense oligodeoxynucleotides and their analogues for inhibition of gene expression (Zamecnik et al. (1978) *Proc. Natl. Acad. Sci. (USA)* 75:280–284). An antisense oligonucleotide targeted at a gene involved in the neoplastic cell growth should specifically interfere only with the expression of that gene, resulting in arrest of cancer cell growth. The ability to specifically block or down-regulate expression of such genes provides a powerful tool to explore the molecular basis of normal growth regulation, as well as the opportunity for therapeutic intervention (see, e.g., Cho-Chung (1993) *Curr. Opin. Thera. Patents* 3:1737–1750). The identification of genes that confer a growth advantage to neoplastic cells as well as other genes causally related to cancer and the understanding of the genetic mechanism(s) responsible for their activation makes the antisense approach to cancer treatment possible.

One such gene encodes the $RI_\alpha$ subunit of cyclic AMP (cAMP)-dependent protein kinase A (PKA) (Krebs (1972) *Curr. Topics Cell. Regul.* 5:99–133). Protein kinase is bound by cAMP, which is thought to have a role in the control of cell proliferation and differentiation (see, e.g., Cho-Chung (1980) *J. Cyclic Nucleotide Res.* 6:163–167). There are two types of PKA, type I (PKA-I) and type II (PKA-II), both of which share a common C subunit but each containing distinct R subunits, RI and RII, respectively (Beebe et al. in *The Enzymes: Control by Phosphorylation*, 17(A):43–111 (Academic, New York, 1986). The R subunit isoforms differ in tissue distribution (Øyen et al. (1988) *FEBS Lett.* 229:391–394; Clegg et al. (1988) *Proc. Natl. Acad. Sci. (USA)* 85:3703–3707) and in biochemical properties (Beebe et al. in *The Enzymes: Control by Phosphorylation*, 17(A):43–111 (Academic Press, NY, 1986); Cadd et al. (1990) *J. Biol. Chem.* 265:19502–19506). The two general isoforms of the R subunit also differ in their subcellular localization: RI is found throughout the cytoplasm; whereas RII localizes to nuclei, nucleoli, Golgi apparatus and the microtubule-organizing center (see, e.g., Lohmann in *Advances in Cyclic Nucleotide and Protein Phosphorylation Research*, 18:63–117 (Raven, New York, 1984; and Nigg et al. (1985) *Cell* 41:1039–1051).

An increase in the level of $RI_\alpha$ expression has been demonstrated in human cancer cell lines and in primary tumors, as compared with normal counterparts, in cells after transformation with the Ki-ras oncogene or transforming growth factor-$\alpha$, and upon stimulation of cell growth with granulocyte-macrophage colony-stimulating factor (GM-CSF) or phorbol esters (Lohmann in *Advances in Cyclic Nucleotide and Protein Phosphorylation Research*, 18:63–117 (Raven, New York, 1984); and Cho-Chung (1990) *Cancer Res.* 50:7093–7100). Conversely, a decrease in the expression of $RI_\alpha$ has been correlated with growth inhibition induced by site-selective cAMP analogs in a broad spectrum of human cancer cell lines (Cho-Chung (1990) *Cancer Res.* 50:7093–7100). It has also been determined that the expression of RI/PKA-I and RII/PKA-II has an inverse relationship during ontogenic development and cell differentiation (Lohmann in *Advances in Cyclic Nucleotide and Protein Phosphorylation Research*, Vol. 18, 63–117 (Raven, New York, 1984); Cho-Chung (1990) *Cancer Res.* 50:7093–7100). The $RI_\alpha$ subunit of PKA has thus been hypothesized to be an ontogenic growth-inducing protein whose constitutive expression disrupts normal ontogenic processes, resulting in a pathogenic outgrowth, such as malignancy (Nesterova et al. (1995) *Nature Medicine* 1:528–533).

Antisense oligonucleotides directed to the $RI_\alpha$ gene have been prepared. U.S. Pat. No. 5,271,941 describes phosphodiester-linked antisense oligonucleotides complementary to a region of the first 100 N-terminal amino acids of $RI_\alpha$ which inhibit the expression of $RI_\alpha$ in leukemia cells in vitro. In addition, antisense phosphorothioate oligodeoxynucleotides corresponding to the N-terminal 8–13 codons of the $RI_\alpha$ gene was found to reduce in vivo tumor growth in nude mice (Nesterova et al. (1995) *Nature Med.* 1:528–533).

Unfortunately, problems have been encountered with the use of phosphodiester-linked (PO) oligonucleotides and some phosphorothioate-linked (PS) oligonucleotides. It is known that nucleases in the serum readily degrade PO oligonucleotides. Replacement of the phosphodiester internucleotide linkages with phosphorothioate internucleotide linkages has been shown to stabilize oligonucleotides in cells, cell extracts, serum, and other nuclease-containing solutions (see, e.g., Bacon et al. (1990) *Biochem. Biophys.*

Meth. 20:259) as well as in vivo (Iversen (1993) *Antisense Research and Application* (Crooke, ed) CRC Press, 461). However, some PS oligonucleotides have been found to exhibit an immunostimulatory response, which in certain cases may be undesirable. For example, Galbraith et al. (*Antisense Res. & Dev.* (1994) 4:201–206) disclose complement activation by some PS oligonucleotides. Henry et al. (*Pharm. Res.* (1994) 11: PPDM8082) disclose that some PS oligonucleotides may potentially interfere with blood clotting.

There is, therefore, a need for modified oligonucleotides directed to cancer-related genes that retain gene expression inhibition properties while producing fewer side effects than conventional oligonucleotides.

SUMMARY OF THE INVENTION

The present invention relates to modified oligonucleotides useful for studies of gene expression and for the antisense therapeutic approach. The invention provides modified oligonucleotides that down-regulate the expression of the $RI_\alpha$ gene while producing fewer side effects than conventional oligonucleotides. In particular, the invention provides modified oligonucleotides that demonstrate reduced mitogenicity, reduced activation of complement and reduced antithrombotic properties, relative to conventional oligonucleotides.

It is also known that some PS oligonucleotides cause an immunostimulatory response in subjects to whom they have been administered, which may be undesirable in some cases.

It is known that exclusively phosphodiester- or exclusively phosphorothioate-linked oligonucleotides directed to the first 100 nucleotides of the $RI_\alpha$ nucleic acid inhibit cell proliferation.

It has now been discovered that modified oligonucleotides complementary to the protein kinase A $RI_\alpha$ subunit gene inhibit the growth of tumors in vivo. With at least the activity of a comparable PO- or PS-linked oligonucleotide with fewer side effects.

This finding has been exploited to produce the present invention, which in a first aspect, includes synthetic hybrid, inverted hybrid, and inverted chimeric oligonucleotides and compositions of matter for specifically down-regulating protein kinase A subunit $RI_\alpha$ gene expression with reduced side effects. Such inhibition of gene expression is useful as an alternative to mutant analysis for determining the biological function and role of protein kinase A-related genes in cell proliferation and tumor growth. Such inhibition of $RI_\alpha$ gene expression can also be used to therapeutically treat diseases and disorders that are caused by the overexpression or inappropriate expression of the gene.

As used herein, the term "synthetic oligonucleotide" includes chemically synthesized polymers of three up to 50, preferably from about 15 to about 30, and most preferably, 18 ribonucleotide and/or deoxyribonucleotide monomers connected together or linked by at least one, and preferably more than one, 5' to 3' internucleotide linkage.

For purposes of the invention, the term "oligonucleotide sequence that is complementary to a genomic region or an RNA molecule transcribed therefrom" is intended to mean an oligonucleotide that binds to the nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, causing pseudoknot formation. Binding by Watson-Crick or Hoogsteen base pairing under physiological conditions is measured as a practical matter by observing interference with the function of the nucleic acid sequence.

In one preferred embodiment according to this aspect of the invention, the oligonucleotide is a core region hybrid oligonucleotide comprising a region of at least two deoxyribonucleotides, flanked by 5' and 3' ribonucleotide regions, each having at least four ribonucleotides. A hybrid oligonucleotide having the sequence set forth in the Sequence Listing as SEQ ID NO:4 is one particular embodiment. In some embodiments, each of the 3' and 5' flanking ribonucleotide regions of an oligonucleotide of the invention comprises at least four contiguous, 2'-O-substituted ribonucleotides.

For purposes of the invention, the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group, but not with a 2'-H group.

In some embodiments, each of the 3' and 5' flanking ribonucleotide regions of an oligonucleotide of the invention comprises at least one 2'-O-alkyl substituted ribonucleotide. In one preferred embodiment, the 2'-O-alkyl-substituted nucleotide is a 2'-O-methyl ribonucleotide. In other preferred embodiments, the 3' and 5' flanking ribonucleotide regions of an oligonucleotide of the invention comprises at least four 2'-O-methyl ribonucleotides. In preferred embodiments, the ribonucleotides and deoxyribonucleotides of the hybrid oligonucleotide are linked by phosphorothioate internucleotide linkages. In particular embodiments, this phosphorothioate region or regions have from about four to about 18 nucleosides joined to each other by 5' to 3' phosphorothioate linkages, and preferably from about 5 to about 18 such phosphorothioate-linked nucleosides. The phosphorothioate linkages may be mixed $R_p$ and $S_p$ enantiomers, or they may be stereoregular or substantially stereoregular in either $R_p$ or $S_p$ form (see Iyer et al. (1995) *Tetrahedron Asymmetry* 6:1051–1054).

In another preferred embodiment according to this aspect of the invention, the oligonucleotide is an inverted hybrid oligonucleotide comprising a region of at least four ribonucleotides flanked by 3' and 5' deoxyribonucleotide regions of at least two deoxyribonucleotides. The structure of this oligonucleotide is "inverted" relative to traditional hybrid oligonucleotides. In some embodiments, the 2'-O-substituted RNA region has from about four to about ten 2'-O-substituted nucleosides joined to each other by 5' to 3' internucleoside linkages, and most preferably from about four to about six such 2'-O-substituted nucleosides. In some embodiments, the oligonucleotides of the invention have a ribonucleotide region that comprises at least five contiguous ribonucleotides. In one particularly preferred embodiment, the overall size of the inverted hybrid oligonucleotide is 18. In preferred embodiments, the 2'-O-substituted ribonucleosides are linked to each other through a 5' to 3' phosphorothioate, phosphorodithioate, phosphotriester, or phosphodiester linkages. The phosphorothioate 3' or 5' flanking region (or regions) has from about four to about 18 nucleosides joined to each other by 5' to 3' phosphorothioate linkages, and preferably from about 5 to about 18 such phosphorothioate-linked nucleosides. In preferred embodiments, the phosphorothioate regions will have at least 5 phosphorothioate-linked nucleosides. One specific embodiment is an oligonucleotide having substantially the nucleotide sequence set forth in the Sequence Listing as SEQ ID NO:6. In preferred embodiments of this aspect of the invention, the ribonucleotide region comprises 2'-O-substituted ribonucleotides, such as 2'-O-alkyl substituted ribonucleotides. One particularly preferred embodiment is an inverted hybrid oligonucleotide whose ribonucleotide region comprises at least one 2'-O-methyl ribonucleotide.

In some embodiments, all of the nucleotides in the inverted hybrid oligonucleotide are linked by phosphorothioate internucleotide linkages. In particular embodiments, the deoxyribonucleotide flanking region or regions has from about four to about 18 nucleosides joined to each other by 5' to 3' phosphorothioate linkages, and preferably from about 5 to about 18 such phosphorothioate-linked nucleosides. In some embodiments, the deoxyribonucleotide 3' and 5' flanking regions of the inverted hybrid oligonucleotides of the invention have about 5 phosphorothioate-linked nucleosides. The phosphorothioate linkages may be mixed $R_p$ and $S_p$ enantiomers, or they may be stereoregular or substantially stereoregular in either $R_p$ or $S_p$ form (see Iyer et al. (1995) *Tetrahedron Asymmetry* 6:1051–1054)

Another embodiment is a composition of matter for inhibiting the expression of protein kinase A subunit $RI_\alpha$ with reduced side effects, the composition comprising an inverted hybrid oligonucleotide according to the invention.

Yet another preferred embodiment according to this aspect of the invention is an inverted chimeric oligonucleotide comprising an oligonucleotide nonionic region of at least four nucleotides flanked by one or more, and preferably two oligonucleotide phosphorothioate regions. Such a chimeric oligonucleotide has a structure that is "inverted" relative to traditional chimeric oligonucleotides. In one particular embodiment, an inverted chimeric oligonucleotide of the invention has substantially the nucleotide sequence set forth in the Sequence Listing as SEQ ID NO:1. In preferred embodiments, the oligonucleotide nonionic region comprises about four to about 12 nucleotides joined to each other by 5' to 3' nonionic linkages. In some embodiments, the nonionic region contains alkylphosphonate and/or phosphoramidate and/or phosphotriester internucleoside linkages. In one particular embodiment, the oligonucleotide nonionic region comprises six nucleotides. In some preferred embodiments, the oligonucleotide has a nonionic region having from about six to about eight methylphosphonate-linked nucleosides, flanked on either side by phosphorothioate regions, each having from about six to about ten phosphorothioate-linked nucleosides. In preferred embodiments, the flanking region or regions are phosphorothioate nucleotides. In some embodiments, the flanking region or regions have from about four to about 24 nucleosides joined to each other by 5' to 3' phosphorothioate linkages, and preferably from about six to about 16 such phosphorothioate-linked nucleosides. In preferred embodiments, the phosphorothioate regions have from about five to about 15 phosphorothioate-linked nucleosides. The phosphorothioate linkages may be mixed $R_p$ and $S_p$ enantiomers, or they may be stereoregular or substantially stereoregular in either $R_p$ or $S_p$ form (see Iyer et al. (1995) *Tetrahedron Asymmetry* 6:1051–1054).

Another embodiment of this aspect of the invention is a composition of matter for inhibiting the expression of protein kinase A subunit $RI_\alpha$ with reduced side effects, the composition comprising an inverted chimeric oligonucleotide according to the invention.

Another aspect of the invention is a method of inhibiting the proliferation of cancer cells in vitro. In this method, an oligonucleotide of the invention is administered to the cells.

Yet another aspect is a therapeutic composition comprising an oligonucleotide of the invention in a pharmaceutically acceptable carrier.

A method of treating cancer in an afflicted subject with reduced side effects is another aspect of the invention. This method comprises administering a therapeutic composition of the invention to the subject in which the protein kinase A subunit $RI_\alpha$ gene is being over-expressed.

Those skilled in the art will recognize that the elements of these preferred embodiments can be combined and the inventor does contemplate such combination. For example, 2'-O-substituted ribonucleotide regions may well include from one to all nonionic internucleoside linkages. Alternatively, nonionic regions may have from one to all 2'-O-substituted ribonucleotides. Moreover, oligonucleotides according to the invention may contain combinations of one or more 2'-O-substituted ribonucleotide region and one or more nonionic region, either or both being flanked by phosphorothioate regions. (See *Nucleosides & Nucleotides* 14:1031–1035 (1995) for relevant synthetic techniques.)

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1 is a graphic representation showing the effect of modified oligonucleotides of the invention on tumor size in a mouse relative to various controls.

DESCRIPTION OF THE PREFERRED EMBODIMENT

The patent and scientific literature referred to herein establishes the knowledge that is available to those with skill in the art. The issued U.S. patents, allowed applications, published foreign applications, and references cited herein are hereby incorporated by reference.

Synthetic oligonucleotides of the hybrid, inverted hybrid, and inverted chimeric oligonucleotides as described above.

Such synthetic hybrid, inverted hybrid, and inverted chimeric oligonucleotides of the invention have a nucleotide sequence complementary to a genomic region or an RNA molecule transcribed therefrom encoding the $RI_\alpha$ subunit of PKA. These oligonucleotides are about 15 to about 30 nucleotides in length, preferably about 15 to 25 nucleotides in length, but most preferably, are about 18 nucleotides long. The sequence of this gene is known. Thus, an oligonucleotide of the invention can have any nucleotide sequence complementary to any region of the gene. Three non-limiting examples of an 18mer of the invention has the sequence set forth below in TABLE 1 as SEQ ID NOS:1, 4, and 6.

TABLE 1

| Oligo # | Sequence (5' → 3') | Type | SEQ ID NO: |
|---|---|---|---|
| 164 | GCG TGC CTC CTC ACT GGC | Antisense | 1 |
| 167 | GCG CGC CTC CTC GCT GGC | Mismatched Control | 2 |
| 188 | GCA TGC TTC CAC ACA GGC | Mismatched Control | 3 |
|  | \*\*\* \*          \* \*\*\* |  |  |
| 165 | GCG UGC CTC CTC ACU GGC | Hybrid | 4 |
|  | \*\*\* \*          \* \*\*\* |  |  |
| 168 | GCG CGC CTC CTC GCU GGC | Mismatched Hybrid (Control) | 5 |
|  |        \*\*\* \*\* |  |  |
| 166 | GCG TGC CUC CUC ACT GGC | Inverted Hybrid | 6 |
|  |        \*\*\* \*\* |  |  |
| 169 | GCG CGC CUC CUC GCT GGC | Mismatched Inverted Hybrid (Control) | 7 |
|  |        \*\*\* \*\* |  |  |
| 189 | GCA TGC AUC CGC ACA GGC | Mismatched Inverted Hybrid (Control) | 8 |
|  |        ••• ••• |  |  |
| 190 | GCG TGC CTC CTC ACT GGC | Inverted Chimeric | 1 |
|  |        ••• ••• |  |  |
| 191 | GCG CGC CTC CTC GCT GGC | Mismatched Inverted Chimeric (Control) | 2 |

X = mismatched bases
\* ribonucleotide
• methylphosphonate nucleotide

Oligonucleotides having greater than 18 oligonucleotides are also contemplated by the invention. These oligonucleotides have up to 25 additional nucleotides extending from the 3', or 5' terminus, or from both the 3' and 5' termini of, for example, the 18mer with SEQ ID NOS:1, 4, or 6, without diminishing the ability of these oligonucleotides to down regulate $RI_\alpha$ gene expression. Alternatively, other oligonucleotides of the invention may have fewer nucleotides than, for example, oligonucleotides having SEQ ID NOS:1, 4, or 6. Such shortened oligonucleotides maintain at least the antisense activity of the parent oligonucleotide to down-regulate the expression of the $RI_\alpha$ gene, or have greater activity.

The oligonucleotides of the invention can be prepared by art recognized methods. Oligonucleotides with phosphorothioate linkages can be prepared manually or by an automated synthesizer and then processed using methods well known in the field such as phosphoramidite (reviewed in Agrawal et al. (1992) *Trends Biotechnol.* 10:152–158, see, e.g., Agrawal et al. (1988) *Proc. Natl. Acad. Sci.* (USA) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used. Examples of other chemical groups include alkylphosphonates, phosphorodithioates, alkylphosphonothioates, phosphoramidates, 2'-O-methyls, carbamates, acetamidate, carboxymethyl esters, carbonates, and phosphate triesters. Oligonucleotides with these linkages can be prepared according to known methods (see, e.g., Goodchild (1990) *Bioconjugate Chem.* 2:165–187; Agrawal et al. (*Proc. Natl. Acad. Sci.* (USA) (1988) 85:7079–7083); Uhlmann et al. (*Chem. Rev.* (1990) 90:534–583); and Agrawal et al. (*Trends Biotechnol.* (1992) 10:152–158)).

Preferred hybrid, inverted hybrid, and inverted chimeric oligonucleotides of the invention may have other modifications which do not substantially affect their ability to specifically down-regulate $RI_\alpha$ gene expression. These modifications include those which are internal or are at the end(s) of the oligonucleotide molecule and include additions to the molecule at the internucleoside phosphate linkages, such as cholesteryl or diamine compounds with varying numbers of carbon residues between the two amino groups, and terminal ribose, deoxyribose and phosphate modifications which cleave, or crosslink to the opposite chains or to associated enzymes or other proteins which bind to the $RI_\alpha$ nucleic acid. Examples of such oligonucleotides include those with a modified base and/or sugar such as arabinose instead of ribose, or a 3',5'-substituted oligonucleotide having a sugar which, at one or both its 3' and 5' positions is attached to a chemical group other than a hydroxyl or phosphate group (at its 3' or 5' position). Other modified oligonucleotides are capped with a nuclease resistance-conferring bulky substituent at their 3' and/or 5' end(s), or have a substitution in one or both nonbridging oxygens per nucleotide. Such modifications can be at some or all of the internucleoside linkages, as well as at either or both ends of the oligonucleotide and/or in the interior of the molecule (reviewed in Agrawal et al. (1992) *Trends Biotechnol.* 10:152–158).

The invention also provides therapeutic compositions suitable for treating undesirable, uncontrolled cell proliferation or cancer comprising at least one oligonucleotide in accordance with the invention, capable of specifically down-regulating expression of the $RI_\alpha$ gene, and a pharmaceutically acceptable carrier or diluent. It is preferred that an oligonucleotide used in the therapeutic composition of the invention be complementary to at least a portion of the $RI_\alpha$ genomic region, gene, or RNA transcript thereof.

As used herein, a "pharmaceutically or physiologically acceptable carrier" includes any and all solvents (including but not limited to lactose), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

Several preferred therapeutic compositions of the invention suitable for inhibiting cell proliferation in vitro or in vivo or for treating cancer in humans in accordance with the methods of the invention comprise about 25 to 75 mg of a lyophilized oligonucleotide(s) having SEQ ID NOS:1, 4, and/or 6 and 20–75 mg lactose, USP, which is reconstituted with sterile normal saline to the therapeutically effective dosages described herein.

The invention also provides methods for treating humans suffering from disorders or diseases wherein the $RI_\alpha$ gene is incorrectly or over-expressed. Such a disorder or disease that could be treated using this method includes tumor-forming cancers such as, but not limited to, human colon carcinoma, breast carcinoma, gastric carcinoma, and neuroblastoma. In the method of the invention, a therapeutically effective amount of a composition of the invention is administered to the human. Such methods of treatment according to the invention, may be administered in conjunction with other therapeutic agents.

As used herein, the term "therapeutically effective amount" means the total amount of each active component of the pharmaceutical formulation or method that is sufficient to show a meaningful subject or patient benefit, i.e., a reduction in tumor growth or in the expression of proteins which cause or characterize the cancer. When applied to an individual active ingredient, administered alone, the term refers to that ingredient alone. When applied to a combination, the term refers to combined amounts of the active ingredients that result in the therapeutic effect, whether administered in combination, serially or simultaneously.

A "therapeutically effective manner" refers to a route, duration, and frequency of administration of the pharmaceutical formulation which ultimately results in meaningful patient benefit, as described above. In some embodiments of the invention, the pharmaceutical formulation is administered via injection, sublingually, rectally, intradermally, orally, or enterally in bolus, continuous, intermittent, or continuous, followed by intermittent, regimens.

The therapeutically effective amount of synthetic oligonucleotide in the pharmaceutical composition of the present invention will depend upon the nature and severity of the condition being treated, and on the nature of prior treatments which the patient has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the dosages of the pharmaceutical compositions administered in the method of the present invention should contain about 0.1 to 5.0 mg/kg body weight per day, and preferably 0.1 to 2.0 mg/kg body weight per day. When administered systemically, the therapeutic composition is preferably administered at a sufficient dosage to attain a blood level of oligonucleotide from about 0.01 $\mu$M to about 10 $\mu$M. Preferably, the concentration of oligonucleotide at the site of aberrant gene expression should be from about 0.01 $\mu$M to about 10 $\mu$M, and most preferably from about 0.05 $\mu$M to about 5 $\mu$M. However, for localized administration, much lower concentrations than this may be effective, and much higher concentrations may be tolerated. It may be desirable to administer simultaneously or sequentially a therapeutically effective amount of one or more of the therapeutic compositions of the invention to an individual as a single treatment episode.

Administration of pharmaceutical compositions in accordance with the invention or to practice the method of the present invention can be carried out in a variety of conventional ways, such as by oral ingestion, enteral, rectal, or transdermal administration, inhalation, sublingual administration, or cutaneous, subcutaneous, intramuscular, intraocular, intraperitoneal, or intravenous injection, or any other route of administration known in the art for administrating therapeutic agents.

When the composition is to be administered orally, sublingually, or by any non-injectable route, the therapeutic formulation will preferably include a physiologically acceptable carrier, such as an inert diluent or an assimilable edible carrier with which the composition is administered. Suitable formulations that include pharmaceutically acceptable excipients for introducing compounds to the bloodstream by other than injection routes can be found in *Remington's Pharmaceutical Sciences* (18th ed.) (Genarro, ed. (1990) Mack Publishing Co., Easton, Pa.). The oligonucleotide and other ingredients may be enclosed in a hard or soft shell gelatin capsule, compressed into tablets, or incorporated directly into the individual's diet. The therapeutic compositions may be incorporated with excipients and used in the form of ingestible tablets, buccal tablets, troches, capsules, elixirs, suspensions, syrups, wafers, and the like. When the therapeutic composition is administered orally, it may be mixed with other food forms and pharmaceutically acceptable flavor enhancers. When the therapeutic composition is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are also contemplated such as those described in U.S. Pat. Nos. 4,704,295, 4,556,552, 4,309,404, and 4,309,406.

When a therapeutically effective amount of composition of the invention is administered by injection, the synthetic oligonucleotide will preferably be in the form of a pyrogen-free, parenterally-acceptable, aqueous solution. The preparation of such parenterally-acceptable solutions, having due regard to ph, isotonicity, stability, and the like, is within the skill in the art. A preferred pharmaceutical composition for injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacteria and fungi. The carrier can be a solvent or dispersion medium. The prevention of the action of microorganisms can be brought about by various antibacterial and antifungal agents. Prolonged absorption of the injectable therapeutic agents can be brought about by the use of compositions of agents delaying absorption. Sterile injectable solutions are prepared by incorporating the oligonucleotide in the required amount in the appropriate solvent, followed by filtered sterilization.

The pharmaceutical formulation can be administered in bolus, continuous, or intermittent dosages, or in a combination of continuous and intermittent dosages, as determined by the physician and the degree and/or stage of illness of the patient. The duration of therapy using the pharmaceutical composition of the present invention will vary, depending on the unique characteristics of the oligonucleotide and the particular therapeutic effect to be achieved, the limitations inherent in the art of preparing such a therapeutic formulation for the treatment of humans, the severity of the disease being treated and the condition and potential idiosyncratic response of each individual patient. Ultimately the attending physician will decide on the appropriate duration of intravenous therapy using the pharmaceutical composition of the present invention.

Compositions of the invention are useful for inhibiting or reducing the proliferation of cancer or tumor cells in vitro. A synthetic oligonucleotide of the invention is administered to the cells in an amount sufficient to enable the binding of the oligonucleotide to a complementary genomic region or RNA molecule transcribed therefrom encoding the $RI_\alpha$ subunit. In this way, expression of PKA is decreased, thus inhibiting or reducing cell proliferation.

Compositions of the invention are also useful for treating cancer or uncontrolled cell proliferation in humans. In this method, a therapeutic formulation including an antisense oligonucleotide of the invention is provided in a physiologically acceptable carrier. The individual is then treated with the therapeutic formulation in an amount sufficient to enable the binding of the oligonucleotide to the PKA $RI_\alpha$ genomic region or RNA molecule transcribed therefrom in the infected cells. In this way, the binding of the oligonucleotide inhibits or down-regulates $RI_\alpha$ expression and hence the activity of PKA.

In practicing the method of treatment or use of the present invention, a therapeutically effective amount of at least one or more therapeutic compositions of the invention is administered to a subject afflicted with a cancer. An anticancer response showing a decrease in tumor growth or size or a decrease in $RI_\alpha$ expression is considered to be a positive indication of the ability of the method and pharmaceutical formulation to inhibit or reduce cell growth and thus, to treat cancer in humans.

At least one therapeutic composition of the invention may be administered in accordance with the method of the invention either alone or in combination with other known therapies for cancer such as cisplatin, carboplatin, paclitaxel, tamoxifen, taxol, interferon α and doxorubicin. When co-administered with one or more other therapies, the compositions of the invention may be administered either simultaneously with the other treatment(s), or sequentially. If administered sequentially, the attending physician will decide on the appropriate sequence of administering the compositions of the invention in combination with the other therapy.

The following examples illustrate the preferred modes of making and practicing the present invention, but are not meant to limit the scope of the invention since alternative methods may be utilized to obtain similar results.

EXAMPLE 1

Synthesis, Deprotection, and Purification of Oligonucleotides

Oligonucleotides were synthesized using standard phosphoramidite chemistry (Beaucage (1993) *Meth. Mol. Biol.* 20:33–61) on an automated DNA synthesizer (Model 8700, Biosearch, Bedford, Mass.) using a beta-cyanoethyl phosphoramidate approach.

Oligonucleotide phosphorothioates were synthesized using an automated DNA synthesizer (Model 8700, Biosearch, Bedford, Mass.) using a beta-cyanoethyl phosphoramidate approach on a 10 micromole scale. To generate the phosphorothioate linkages, the intermediate phosphite linkage obtained after each coupling was oxidized using 3H, 1,2-benzodithiole-3H-one-1,1-dioxide (see Beaucage, in *Protocols for Oligonucleotides and Analogs: Synthesis and Properties,* Agrawal (ed.), (1993) Humana Press, Totowa, N.J., pp. 33–62). Similar synthesis was carried out to generate phosphodiester linkages, except that a standard oxidation was carried out using standard iodine reagent. Synthesis of inverted chimeric oligonucleotide was carried out in the same manner, except that methylphosphonate linkages were assembled using nucleoside methylphosphonamidite (Glen Research, Sterling, Va.), followed by oxidation with 0.1 M iodine in tetrahydrofuran/2,6-lutidine/water (75:25:0.25) (see Agrawal & Goodchild (1987) *Tet. Lett.* 28:3539–3542). Hybrids and inverted hybrid oligonucleotides were synthesized similarly, except that the segment containing 2'-O-methylribonucleotides was assembled using 2'-O-methylribonucleoside phosphoramidite, followed by oxidation to a phosphorothioate or phosphodiester linkage as described above. Deprotection and purification of oligonucleotides was carried out according to standard procedures, (see Padmapriya et al. (1994) *Antisense Res. & Dev.* 4:185–199), except for oligonucleotides containing methylphosphonate-containing regions. For those oligonucleotides, the CPG-bound oligonucleotide was treated with concentrated ammonium hydroxide for 1 hour at room temperature, and the supernatant was removed and evaporated to obtain a pale yellow residue, which was then treated with a mixture of ethylenediamine/ethanol (1:1 v/v) for 6 hours at room temperature and dried again under reduced pressure.

EXAMPLE 2

In Vitro Complement Activation Studies

The cell line utilized was the CEM-SS cell line (Southern Research Institute-Frederick Research Center, Frederick, Md.). These cells are highly susceptible to infection with HIV, rapidly form multinucleated syncytia, and are eventually killed by HIV. The cells were maintained ($2-7 \times 10^5$ cells per ml) in RPMI 1640 tissue culture medium supplementd with 10% fetal bovine serum, glutamine, and antibiotics, and were passaged twice weekly at 1:20 dilution. Passage number was logged each week. Cells were discarded after twenty weeks of passage and fresh CEM-SS cells thawed and utilized in the assay. Stocks of CEM-SS cells were frozen in liquid nitrogen in 1 ml NUNC vials in 90% fetal calf serum and 10% dimethyl sulfoxide (DMSO). Following thawing, CEM-SS cells were routinely ready to be utilized in the primary screen assay after two weeks in culture. Prior to replacing a late passage cell line, the new CEM-SS cells were tested in the screening assay protocol utilizing the current stock of infectious virus and AZT. If the infectivity of the virus was significantly different on the new cells or if AZT appeared less active than expected the new cells were not entered into the screening program. Mycoplasma testing was routinely performed on all cell lines.

Titer determinations included reverse transcriptase activity assay (see methods below), endpoint titration or plaque assay (CEM-SS) quantification of infectious particles (see methods below), and quantification of cell killing kinetics.

ELISA kits were purchased from Coulter. The assay is performed according to the manufacturer's recommendations. Prior to ELISA analysis we routinely performed the reverse transcriptase activity assays (described above) and used the values for incorporated radioactivity in the RT activity assay to determine the dilution of our samples required for the ELISA. We have constructed standard curves so that the dilutions of virus to be used in the p24 ELISA can be accurately determined from the RT activity assay. Control curves are generated in each assay to accurately quantify the amount of capsid protein in each sample. Data was obtained by spectrophotometric analysis at 450 nm using a Molecular Devices Vmax plate reader. P24 concentrations were calculated from the optical density values by use of the Molecular Devices software package Soft Max.

Infectious virus particles were quantified utilizing the CEM-SS plaque assay as described by Nara, P. L. and Fischinger, P. J. (1988) Quantitative infectivity assay for HIV-1 and HIV-2 *Nature* 332:469–470). Flat bottom 96-well microtiter plates (Costar) were coated with 50 μl of poly-L-lysine (Sigma) at 50 μg/ml for 2 hours at 37° C. The wells were then washed with PBS and $2.5 \times 10^5$ CEM-SS cells were placed in the microtiter well where they became fixed to the bottom of the plate. Enough cells were added to form a monolayer of CEM-SS cells in each well. Virus containing supernatant was added from each well of the XTT plate, including virus and cell controls and each serial dilution of the test substance. The number of syncytia were quantified in the flat-bottom 96-well microtiter plate with an Olympus CK2 inverted microscope at 4 days following infection. Each syncytium resulted from a single infectious HIV virion.

To determine the relative effect of inverted hybrid or inverted chimeric structure on oligonucleotide-mediated depletion of complement, the following experiments were performed. Venous blood was collected from healthy adult human volunteers. Serum was prepared for hemolytic complement assay by collecting blood into vacutainers (Becton Dickinson #6430 Franklin Lakes, N.J.) without commercial additives. Blood was allowed to clot at room temperature for 30 minutes, chilled on ice for 15 minutes, then centrifuged at 4° C. to separate serum. Harvested serum was kept on ice for same day assay or, alternatively, stored at −70° C. Buffer, or an oligonucleotide sample was then incubated with the serum. The oligonucleotides tested were 25mer oligonucleotide phosphodiesters or phosphorothioates, 25mer hybrid oligonucleotides, 25mer inverted hybrid oligonucleotides, 25mer chimeric oligonucleotides, and 25mer inverted chimeric oligonucleotides. Representative hybrid oligonucleotides were composed of seven to 13 2'-O-methyl ribonucleotides flanked by two regions of six to nine deoxyribonucleotides each. Representative 25mer inverted hybrid oligonucleotides were composed of 17 deoxyribonucleotides flanked by two regions of four ribonucleotides each. Representative 25mer chimeric oligonucleotides were composed of six methylphosphonate deoxyribonucleotides and 19 phosphorothioate deoxyribonucleotides. Representative inverted chimeric oligonucleotides were composed of from 16 to 17 phosphorothioate deoxyribonucleotides flanked by regions of from two to seven methylphosphonate deoxyribonucleotides, or from six to eight methylphosphonate deoxyribonucleotides flanked by nine to ten phosphorothioate deoxyribonucleotides, or two phosphorothioate regions ranging from two to 12 oligonucleotides, flanked by three phosphorothioate regions ranging in size from two to six nucleotides in length. A standard CH50 assay (See Kabat and Mayer (eds), *Experimental Immunochemistry*, 2d Ed., Springfield, Ill., C. C. Thomas, p. 125) for complement-mediated lysis of sheep red blood cells (Colorado Serum Co.) sensitized with anti-sheep red blood cell antibody (hemolysin, Diamedix, Miami, Fla.) was performed, using duplicate determinations of at least five dilutions of each test serum, then hemoglobin release into cell-free supernates was measured spectrophotometrically at 541 nm.

EXAMPLE 3

In Vitro Mitogenicity Studies

To determine the relative effect of inverted hybrid or inverted chimeric structure on oligonucleotide-mediated mitogenicity, the following experiments were performed. Spleen was taken from a male CD1 mouse (4–5 weeks, 20–22 g; Charles River, Wilmington, Mass.). Single cell suspensions were prepared by gently mincing with frosted edges of glass slides. Cells were then cultured in RPMI complete media (RPMI media supplemented with 10% fetal bovine serum (FBS), 50 micromolar 2-mercaptoethanol (2-ME), 100 U/ml penicillin, 100 micrograms/ml streptomycin, 2 mM L-glutamine). To minimize oligonucleotide degradation, FBS was first heated for 30 minutes at 65° C. (phosphodiester-containing oligonucleotides) or 56° C. (all other oligonucleotides). Cells were plated in 96 well dishes at 100,000 cells per well (volume of 100 microliters/well). One type of each oligonucleotide described in Example 2 above in 10 microliters TE buffer (10 mM Tris-HCl, pH 7.5, 1 mM EDTA) was added to each well. After 44 hours of culturing at 37° C., one microcurie tritiated thymidine (Amersham, Arlington Heights, Ill.) was added in 20 microliters RPMI media for a 4 hour pulse labelling. The cells were then harvested in an automatic cell harvester (Skatron, Sterling, Va.) and the filters were assessed using a scintillation counter. In control experiments for mitogenicity, cells were treated identically, except that either media (negative control) or concanavalin A (positive control) was added to the cells in place of the oligonucleotides.

All of the inverted hybrid oligonucleotides proved to be less immunogenic than phosphorothioate oligonucleotides. Inverted hybrid oligonucleotides having phosphodiester linkages in the 2'-O-methyl region appeared to be slightly less immunogenic than those containing phosphorothioate linkages in that region. No significant difference in mitogenicity was observed when the 2'-O-methyl ribonucleotide region was pared down from 13 to 11 or to 9 nucleotides. Inverted chimeric oligonucleotides were also generally less mitogenic than phosphorothioate oligonucleotides. In addition, these oligonucleotides appeared to be less mitogenic than traditional chimeric oligonucleotides, at least in cases in which the traditional chimeric oligonucleotides had significant numbers of methylphosphonate linkages near the 3' end. Increasing the number of methylphosphonate linkers in the middle of the oligonucleotide from 5 to 6 or 7 did not appear to have a significant effect on mitogenicity. These results indicate that incorporation of inverted hybrid or inverted chimeric structure into an oligonucleotide can reduce its mitogenicity.

EXAMPLE 4

In Vitro Studies

To determine the relative effect of inverted hybrid or inverted chimeric structure on oligonucleotide-induced mitogenicity, the following experiments were performed. Venous blood was collected from healthy adult human volunteers. Plasma for clotting time assay was prepared by collecting blood into siliconized vacutainers with sodium citrate (Becton Dickinson #367705), followed by two centrifugations at 4° C. to prepare platelet-poor plasma. Plasma aliquots were kept on ice, spiked with various test oligonucleotides described in Example 2 above, and either tested immediately or quickly frozen on dry ice for subsequent storage at −20° C. prior to coagulation assay. Activated partial thromboplastin time (aPTT) was performed in duplicate on an Electra 1000C (Medical Laboratory Automation, Mount Vernon, N.Y.) according to the manufacturer's recommended procedures, using Actin FSL (Baxter Dade, Miami, Fla.) and calcium to initiate clot formation, which was measured photometrically. Prolongation of aPTT was taken as an indication of clotting inhibition side effect produced by the oligonucleotide.

Traditional phosphorothioate oligonucleotides produced the greatest prolongation of aPTT, of all of the oligonucleotides tested. Traditional hybrid oligonucleotides produced somewhat reduced prolongation of aPTT. In comparison with traditional phosphorothioate or traditional hybrid oligonucleotides, all of the inverted hybrid oligonucleotides tested produced significantly reduced prolongation of aPTT. Inverted hybrid oligonucleotides having phosphodiester linkages in the 2'-O-substituted ribonucleotide region had the greatest reduction in this side effect, with one such oligonucleotide having a 2'-O-methyl RNA phosphodiester region of 13 nucleotides showing very little prolongation of aPTT, even at oligonucleotide concentrations as high as 100 micrograms/ml. Traditional chimeric oligonucleotides produce much less prolongation of aPTT than do traditional phosphorothioate oligonucleotides. Generally, inverted chimeric oligonucleotides retain this characteristic. At least one inverted chimeric oligonucleotide, having a methylphosphonate region of seven nucleotides flanked by phosphorothioate regions of nine nucleotides, gave better results in this assay than the traditional chimeric oligonucleotides at all but the highest oligonucleotide concentrations tested. These results indicate that inverted hybrid and inverted chimeric oligonucleotides may provide advantages in reducing the side effect of clotting inhibition when they are administered to modulate gene expression in vivo.

EXAMPLE 5

In Vivo Complement Activation Studies

Rhesus monkeys (4–9 kg body weight) are acclimatized to laboratory conditions for at least 7 days prior to the study. On the day of the study, each animal is lightly sedated with ketamine-HCl (10 mg/kg) and diazepam (0.5 mg/kg). Surgical level anesthesia is induced and maintained by continuous ketamine intravenous drip throughout the procedure. The oligonucleotides described in Example 2 above are dissolved in normal saline and infused intravenously via a cephalic vein catheter, using a programmable infusion pump at a delivery rate of 0.42 mg/minute. For each oligonucleotide, doses of 0, 0.5, 1, 2, 5 and 10 mg/kg are administered to two animals each over a 10 minute infusion period. Arterial blood samples are collected 10 minutes prior to oligonucleotide administration and 2, 5, 10, 20, 40 and 60 minutes after the start of the infusion, as well as 24 hours later. Serum is used for determining complement CH50, using the conventional complement-dependent lysis of sheep erythrocyte procedure (see Kabat and Mayer, 1961, supra). At the highest dose, phosphorothioate oligonucleotide causes a decrease in serum complement CH50 beginning within 5 minutes of the start of infusion. Inverted hybrid and chimeric oligonucleotides are expected to show a much reduced or undetectable decrease in serum complement CH50 under these conditions.

EXAMPLE 6

In Vivo Mitogenicity Studies

CD1 mice are injected intraperitoneally with a dose of 50 mg/kg body weight of oligonucleotide described in Example 2 above. Forty-eight hours later, the animals are euthanized and the spleens are removed and weighed. Animals treated with inverted hybrid or inverted hybrid oligonucleotides are expected to show no significant increase in spleen weight, while those treated with oligonucleotide phosphorothioates are expected to show modest increases in spleen weight.

EXAMPLE 7

In Vivo Clotting Studies

Rhesus monkeys are treated as in Example 5. From the whole blood samples taken, plasma for clotting assay is prepared, and the assay performed, as described in Example 4. It is expected that prolongation of aPTT will be substantially reduced for both inverted hybrid oligonucleotides and for inverted chimeric oligonucleotide, relative to traditional oligonucleotide phosphorothioates.

EXAMPLE 8

RNase H Activity Studies

To determine the ability of inverted hybrid oligonucleotides and inverted chimeric oligonucleotides to activate RNase H when bound to a complementary RNA molecule, the following experiments were performed. Each type of oligonucleotide described in Example 2 above was incubated together with a molar equivalent quantity of complimentary oligoribonucleotide (0.266 micromolar concentration of each), in a cuvette containing a final volume of 1 ml RNase H buffer (20 mM Tris-HCl, pH 7.5, 10 mM $MgCl_2$, 0.1 M KCl, 2% glycerol, 0.1 mM DTT). The samples were heated to 95° C., then cooled gradually to room temperature to allow annealing to form duplexes. Annealed duplexes were incubated for 10 minutes at 37° C., then 5 units RNase H was added and data collection commenced over a three hour period. Data was collected using a spectrophotometer (GBC 920, GBC Scientific Equipment, Victoria, Australia) at 259 nm. RNase H degradation was determined by hyperchromic shift.

As expected, phosphodiester oligonucleotides behaved as very good co-substrates for RNase H-mediated degradation of RNA, with a degradative half-life of 8.8 seconds. Phosphorothioate oligonucleotides produced an increased half-life of 22.4 seconds. Introduction of a 2'-O-methyl ribonucleotide segment at either end of the oligonucleotide further worsened RNase H activity (half-life=32.7 seconds). In contrast, introducing a 2'-O-methyl segment into the middle of the oligonucleotide (inverted hybrid structure) always resulted in improved RNase H-mediated degradation. When a region of 13 2'-O-methylribonucleoside phosphodiesters was flanked on both sides by phosphorothioate DNA, the best RNase H activity was observed, with a half-life of 7.9 seconds. Introduction of large blocks of methylphosphonate-linked nucleosides at the 3' end of the oligonucleotide either had no effect or caused further deterioration of RNase H activity even when in a chimeric configuration. Introduction of methylphosphonate linked nucleosides at the 5' end, however, improved RNase H activity, particularly in a chimeric configuration with a single methylphosphonate linker at the 3' end (best half-life=8.1 seconds). All inverted chimeric oligonucleotides with methylphosphonate core regions flanked by phosphorothioate regions gave good RNase results, with a half-life range of 9.3 to 14.4 seconds. These results indicate that the introduction of inverted hybrid or inverted chimeric structure into phosphorothioate-containing oligonucleotides can restore some or all of the ability of the oligonucleotide to act as a co-substrate for RNase H, a potentially important attribute for an effective antisense agent.

EXAMPLE 9

Melting Temperature Studies

To determine the effect of inverted hybrid or inverted chimeric structure on stability of the duplex formed between an antisense oligonucleotide and a target molecule, the following experiments were performed. Thermal melting (Tm) data were collected using a spectrophotometer (GBC 920, GBC Scientific Equipment, Victoria, Australia), which has six 10 mm cuvettes mounted in a dual carousel. In the Tm experiments, the temperature was directed and controlled through a peltier effect temperature controller by a computer, using software provided by GBC, according to the manufacturer's directions. Tm data were analyzed by both the first derivative method and the mid-point method, as performed by the software. Tm experiments were performed in a buffer containing 10 mM PIPES, pH 7.0, 1 mM EDTA, 1 M NaCl. A refrigerated bath (VWR 1166, VWR, Boston, Mass.) was connected to the peltier-effect temperature controller to absorb the heat oligonucleotide strand concentration was determined using absorbance values at 260 nm, taking into account extinction coefficients.

EXAMPLE 10

Tumor Growth and Antisense Treatment

LS-174T human colon carcinoma cells ($1\times10^6$ cells) were inoculated subcutaneously (s.c.) into the left flank of athymic mice. A single dose of $RI_\alpha$ antisense hybrid (Oligo 165, SEQ ID NO:4), inverted hybrid (Oligo 166, SEQ ID NO:6), or antisense (Oligo 164, SEQ ID NO:1) oligonucleotides or control oligonucleotide (Oligo 169, SEQ ID NO:7); Oligo 168 (SEQ ID NO:5); Oligo 188, (SEQ ID NO:3) as shown in Table 1 (1 mg per 0.1 ml saline per mouse), or saline (0.1 ml per mouse), was injected s.c. into the right flank of mice when tumor size reached 80 to 100 mg, about 1 week after cell inoculation. Tumor volumes were obtained from daily measurement of the longest and shortest diameters and calculation by the formula, $4/3\pi r^3$ where r=(length+width)/ 4. At each indicated time, two animals from the control and antisense-treated groups were killed, and tumors were removed and weighed. The results are shown in FIG. 1. These results show that the size of the tumor in the animal treated with the inverted hybrid oligonucleotide 166 having SEQ ID NO:6 was surprisingly smaller from three days after injection onward than the phosphorothioate oligonucleotide 164 having SEQ ID NO:1. That this effect was sequence-specific is also demonstrated in FIG. 1: control oligonucleotide 168 (SEQ ID NO:5) has little ability to keep tumor size at a minimum relative to the hybrid and inverted hybrid oligonucleotides.

EXAMPLE 11

Photoaffinity Labelling and Immunoprecipitation of $RI_\alpha$ Subunits

The tumors are homogenized with a Teflon/glass homogenizer in ice-cold buffer 10 (Tris-HCl, pH 7.4, 20 mM; NaCl, 100 mM; NP-40, 1%; sodium deoxycholate, 0.5%; $MgCl_2$, 5 mM; pepstatin, 0.1 mM; antipain, 0.1 mM; chymostatin, 0.1 mM; leupeptin, 0.2 mM; aprotinin, 0.4 mg/ml; and soybean trypsin inhibitor, 0.5 mg/ml; filtered through a 0.45-$\mu$m pore size membrane), and centrifuged for 5 min in an Eppendorf microfuge at 4° C. The supernatants are used as tumor extracts.

The amount of PKA $RI_\alpha$ subunits in tumors is determined by photoaffinity labelling with 8-$N_3$-[$^{32}P$] cAMP followed by immunoprecipitation with $RI_\alpha$ antibodies as described by Tortora et al. (*Proc. Natl. Acad. Sci.* (*USA*) (1990) 87:705–708). The photoactivated incorporation of 8-$N_3$-[$^{32}P$] cAMP (60.0 Ci/m-mol), and the immunoprecipitation using the anti-$RI_\alpha$ or anti-$RII_\beta$ antiserum and protein A Sepharose and SDS-PAGE of solubilized antigen-antibody complex follows the method previously described (Tortora et al. (1990) *Proc. Natl. Acad. Sci.* (*USA*) 87:705–708; Ekanger et al. (1985) *J. Biol. Chem.* 260:3393–3401). It is expected that the amount of $RI_\alpha$ in tumors treated with hybrid, inverted hybrid, and inverted chimeric oligonucleotides of the invention will be reduced compared with the amount in tumors treated with mismatch, straight phosphorothioate, or straight phosphodiester oligonucleotide controls, saline, or other controls.

EXAMPLE 12 cAMP-Dependent Protein Kinase Assays

Extracts (10 mg protein) of tumors from antisense-, control antisense-, or saline-treated animals are loaded onto DEAE cellulose columns (1×10 cm) and fractionated with a linear salt gradient (Rohlff et al. (1993) *J. Biol. Chem.* 268:5774–5782). PKA activity is determined in the absence or presence of 5 $\mu$M cAMP as described below (Rohlff et al. (1993) *J. Biol. Chem.* 268:5774–5782). cAMP-binding activity is measured by the method described previously and expressed as the specific binding (Tagliaferri et al. (1988) *J. Biol. Chem.* 263:409–416).

After two washes with Dulbecco's phosphate-buffered saline, cell pellets ($2\times10^6$ cells) are lysed in 0.5 ml of 20 mM Tris (pH 7.5), 0.1 mM sodium EDTA, 1 mm dithiothreitol, 0.1 mM pepstatin, 0.1 mM antipain, 0.1 mM chymostatin, 0.2 mM leupeptin, 0.4 mg/ml aprotinin, and 0.5 mg/ml soybean trypsin inhibitor, using 100 strokes of a Dounce homogenizer. After centrifugation (Eppendorf 5412) for 5 min, the supernatants are adjusted to 0.7 mg protein/ml and assayed (Uhler et al. (1987) *J. Biol. Chem.* 262:15202–15207) immediately. Assays (40 µl total volume) are performed for 10 min at 300° C. and contained 200 µM ATP, 2.7×10⁶ cpm γ [$^{32}$P]ATP, 20 mM MgCl$_2$, 100 µM Kemptide (Sigma K-1127) (Kemp et al. (1977) *J. Biol. Chem.* 252:4888–4894), 40 mM Tris (pH 7.5), ±100 µM protein kinase inhibitor (Sigma P-3294) (Cheng et al. (1985) *Biochem. J.* 231:655–661), ±8 µM cAMP and 7 µg of cell extract. The phosphorylation of Kemptide is determined by spotting 20 µl of incubation mixture on phosphocellulose filters (Whatman, P81) and washing in phosphoric acid as described (Roskoski (1983) Methods Enzymol. 99:3–6). Radioactivity is measured by liquid scintillation using Econofluor-2 (NEN Research Products NEF-969). It is expected that PKA and cAMP binding activity will be reduced in extracts of tumors treated with the hybrid, inverted hybrid, and inverted chimeric oligonucleotides of the invention.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A synthetic, modified oligonucleotide complementary to, and capable of down-regulating the expression of, nucleic acid encoding protein kinase A subunit RIα, the modified oligonucleotide having from about 15 to about 30 nucleotides and being a hybrid, inverted hybrid, or inverted chimeric oligonucleotide, the hybrid oligonucleotide comprising a region of at least two deoxyribonucleotides, flanked by 3' and 5' flanking ribonucleotide regions each having at least four ribonucleotides, the inverted hybrid oligonucleotide comprising a region of at least four ribonucleotides flanked by 3' and 5' flanking deoxyribonucleotide regions of at least two deoxyribonucleotides, and the inverted chimeric oligonucleotide comprising an oligonucleotide nonionic region of at least four nucleotides flanked by two oligonucleotide phosphorothioate regions.

2. The oligonucleotide of claim 1 having 18 nucleotides.

3. The oligonucleotide of claim 1 which is a hybrid oligonucleotide.

4. The oligonucleotide of claim 3 consisting essentially of the nucleotide sequence set forth in SEQ ID NO:4.

5. The oligonucleotide of claim 3, wherein each of the flanking ribonucleotide regions comprises at least four contiguous 2'-O-substituted ribonucleotides.

6. The oligonucleotide of claim 5, wherein each of the flanking ribonucleotide regions comprises at least one 2'-O-alkyl ribonucleotide.

7. The oligonucleotide of claim 6, wherein each of the flanking ribonucleotide regions comprises at least one 2'-O-methyl ribonucleotide.

8. The oligonucleotide of claim 5, wherein each of the flanking ribonucleotide regions comprises at least four 2'-O-methyl ribonucleotides.

9. The oligonucleotide of claim 3, wherein the ribonucleotides and deoxyribonucleotides are linked by phosphorothioate internucleotide linkages.

10. A therapeutic composition comprising the oligonucleotide of claim 3 in a pharmaceutically acceptable carrier.

11. A composition for inhibiting the expression of protein kinase A with reduced mitogenicity, reduced activation of complement, or reduced antithrombotic properties, relative to the side effects caused by an oligonucleotide which is not hybrid, the composition comprising the hybrid oligonucleotide of claim 3.

12. The oligonucleotide of claim 1 which is an inverted hybrid oligonucleotide.

13. The oligonucleotide of claim 12 consisting essentially of the nucleotide sequence set forth in the Sequence Listing as SEQ ID NO:6.

14. The oligonucleotide of claim 12, wherein the ribonucleotide region comprises at least five contiguous ribonucleotides.

15. The oligonucleotide of claim 14, wherein the deoxyribonucleotide flanking regions comprise six contiguous ribonucleotides.

16. The oligonucleotide of claim 12, wherein the flanking ribonucleotide regions comprise 2'-O-substituted ribonucleotides.

17. The oligonucleotide of claim 16, wherein the 2'-O-substituted ribonucleotides are 2'-O-alkyl substituted ribonucleotides.

18. The oligonucleotide of claim 17, wherein each of the flanking ribonucleotide regions comprise at least one 2'-O-methyl ribonucleotide.

19. The oligonucleotide of claim 12, wherein the nucleotides are linked by phosphorothioate internucleotide linkages.

20. A therapeutic composition comprising the oligonucleotide of claim 12 in a pharmaceutically acceptable carrier.

21. The oligonucleotide of claim 1 which is an inverted chimeric oligonucleotide.

22. The oligonucleotide of claim 21 consisting essentially of the nucleotide sequence set forth in the Sequence Listing as SEQ ID NO:1.

23. The oligonucleotide of claim 21, wherein the oligonucleotide nonionic region comprises about 4 to about 12 nucleotides.

24. The oligonucleotide of claim 23, wherein the oligonucleotide nonionic region comprises six nucleotides.

25. The oligonucleotide of claim 21, wherein the oligonucleotide nonionic region comprises alkylphosphonate nucleotides.

26. The oligonucleotide of claim 25, wherein the oligonucleotide nonionic region comprises methylphosphonate nucleotides.

27. The oligonucleotide of claim 21, wherein the nucleotides in the flanking regions comprise at least six contiguous nucleotides linked by phosphorothioate internucleotide linkages.

28. A therapeutic composition comprising the oligonucleotide of claim 21 in a pharmaceutically acceptable carrier.

29. A therapeutic composition comprising the oligonucleotide of claim 1 in a pharmaceutically acceptable carrier.

30. A composition of matter for inhibiting the expression of protein kinase A with reduced mitogenicity, reduced activation of complement, or reduced antithrombotic properties, relative to the side effects caused by an oligonucleotide which is not inverted hybrid, the composition comprising the inverted hybrid oligonucleotide of claim 12.

31. A composition of matter for inhibiting the expression of the protein kinase A $RI_\alpha$ subunit gene with reduced mitogenicity, reduced activation of complement, or reduced antithrombotic properties, relative to the side effects caused by an oligonucleotide which is not an inverted chimeric, the composition comprising the inverted chimeric oligonucleotide of claim 21.

* * * * *